US008054463B2

(12) United States Patent
Morris et al.

(10) Patent No.: US 8,054,463 B2
(45) Date of Patent: Nov. 8, 2011

(54) METHOD AND SYSTEM FOR MEASURING SUB-SURFACE COMPOSITION OF A SAMPLE

(75) Inventors: Michael D. Morris, Ann Arbor, MI (US); William F. Finney, Chicago, IL (US); Matthew Schulmerich, Jackson, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 243 days.

(21) Appl. No.: 12/066,915

(22) PCT Filed: Feb. 23, 2006

(86) PCT No.: PCT/US2006/006533
§ 371 (c)(1),
(2), (4) Date: Oct. 9, 2008

(87) PCT Pub. No.: WO2007/040589
PCT Pub. Date: Apr. 12, 2007

(65) Prior Publication Data
US 2009/0219523 A1    Sep. 3, 2009

Related U.S. Application Data

(60) Provisional application No. 60/717,900, filed on Sep. 16, 2005.

(51) Int. Cl.
*G01N 21/47* (2006.01)
*G01N 21/65* (2006.01)
(52) U.S. Cl. .................. 356/326; 356/301; 250/339.07; 600/310
(58) Field of Classification Search .................. 356/301; 600/310
See application file for complete search history.

(56) References Cited

U.S. PATENT DOCUMENTS 4,379,225 A    4/1983    Apothaker et al.
(Continued)

FOREIGN PATENT DOCUMENTS

DE    10 2004 009 6    6/2005
(Continued)

OTHER PUBLICATIONS

Matousek et al., Subsurface Probing in Diffusely Scattering Media Using Spatially Offset Raman Spectroscopy, Applied Spectroscopy, vol. 59, No. 4, Apr. 1, 2005, pp. 393-400.*

(Continued)

*Primary Examiner* — F. L Evans
(74) *Attorney, Agent, or Firm* — Marshall, Gerstein & Borun LLP (57) ABSTRACT

In a method for measuring a composition of a sample, an illumination surface area of the sample is illuminated using a light source, and light from a plurality of emitting surface areas of the sample is received, each emitting surface area at a different location, the received light scattered by the sample. A cumulative area of the illumination surface area is greater than a cumulative area of two emitting surface areas of the plurality of emitting surface areas. For each emitting surface area, spectral content information associated with received light corresponding to that emitting surface area is determined, and composition information corresponding to a sub-surface region of the sample is determined based on the determined spectral content information. Different shapes of illumination surface areas as well as the plurality of emitting surface areas may advantageously be utilized for various specimen or sample geometries or illumination sources.

48 Claims, 8 Drawing Sheets

U.S. PATENT DOCUMENTS

| | | | |
|---|---|---|---|
| 5,353,799 | A | 10/1994 | Chance et al. |
| 5,452,723 | A | 9/1995 | Wu et al. |
| 5,987,346 | A | 11/1999 | Benaron et al. |
| 6,352,502 | B1 | 3/2002 | Chaiken et al. |
| 6,737,649 | B2 * | 5/2004 | Webster ................ 356/301 |
| 6,754,518 | B1 | 6/2004 | Lloyd et al. |
| 6,850,656 | B1 * | 2/2005 | Bevilacqua et al. ........ 385/12 |
| 6,949,635 | B1 | 9/2005 | Kumar et al. |
| 2002/0002336 | A1 | 1/2002 | Marchitto et al. |
| 2002/0010400 | A1 | 1/2002 | Camacho et al. |
| 2003/0191398 | A1 | 10/2003 | Motz et al. |
| 2003/0220549 | A1 | 11/2003 | Liu et al. |
| 2004/0073120 | A1 | 4/2004 | Motz et al. |
| 2004/0119976 | A1 | 6/2004 | Faupel et al. |
| 2005/0010130 | A1 | 1/2005 | Morris et al. |
| 2005/0119587 | A1 | 6/2005 | Roessler et al. |
| 2007/0049808 | A1 | 3/2007 | Roessler et al. |
| 2008/0076985 | A1 * | 3/2008 | Matousek et al. ........ 600/310 |
| 2008/0129992 | A1 | 6/2008 | Matousek et al. |

FOREIGN PATENT DOCUMENTS

| | | |
|---|---|---|
| GB | 0426993.2 | 12/2004 |
| WO | WO 01/52739 | 7/2001 |
| WO | WO 2006/061565 | 6/2006 |
| WO | WO 2006/061566 | 6/2006 |

OTHER PUBLICATIONS

Written Opinion for International Application No. PCT/US2006/006533, mailed Jun. 28, 2006.

International Search Report for International Application No. PCT/US2006/006533, mailed Jun. 28, 2006.

Abstract of "Subsurface Raman Spectroscopy of Highly Scattering Systems Using a Non-Confocal Fiber Optic Array Probe. Application to Transcutaneous Tissue Spectroscopy," made available on the Internet on Aug. 25, 2005.

Widjaja et al., "Band-Target Entropy Minimization (BTEM) Applied to Hyperspectral Raman Image Data," Applied Spectroscopy, vol. 57, No. 11, pp. 1353-62 (2003).

Motz et al., "Optical fiber Probe for Biomedical Raman Spectroscopy," Applied Optics, vol. 43, No. 3, pp. 542-554 (Jan. 2004).

Bakker Schut et al., "In Vivo Detection of Dysplastic Tissue by Raman Spectroscopy", Analytical Chemistry, vol. 72, No. 24, pp. 6010-6018, Dec. 15, 2000.

Enejder et al., "Raman Spectroscopy for Noninvasive Glucose Measurements", Journal of Biomedical Optics, vol. 10(3), pp. 031114-1 through 031114-9, May/Jun. 2005.

Motz et al., "Real-Time Raman System for in Vivo Disease Diagnosis", Journal of Biomedical Optics, vol. 10(3), pp. 031113-1 through 031113-7, May/Jun. 2005.

Shim et al., "Study of Fiber-Optic Probes for in Vivo Medial Raman Spectroscopy", Applied Spectroscopy, vol. 53, No. 6, pp. 619-627, 1999.

Pfefer et al., "Multiple-Fiber Probe Design for Fluorescence Spectroscopy in Tissue", Applied Optics, vol. 41, No. 22, pp. 4712-4721, Aug. 1, 2002.

Wikström et al., "Comparison of Sampling Techniques for In-Line Monitoring Using Raman Spectroscopy", Applied Spectroscopy, vol. 59, No. 7, pp. 934-941, 2005.

U.S. Appl. No. 60/669,880, filed Apr. 11, 2005, Matousek et al.

Matousek, "Inverse Spatially Offset Raman Spectroscopy for Deep Noninvasive Probing of Turbid Media," Applied Spectroscopy, vol. 60, No. 11, pp. 1341-1347, 2006.

Timlin, et al., "Spatial Distribution of Phosphate Species in Mature and Newly Generated Mammalian Bone by Hyperspectral Raman Imaging," J. of Biomedical Optics, vol. 4, No. 1, pp. 28-34 (Jan. 1999).

Morris, et al., "Kerr-gated Picoseconds Raman Spectroscopy and Raman Photon Migration of Equine Bone Tissue with 400-nm Excitation," Proc. of SPIE, vol. 5321, pp. 164-169 (2004).

Matousek, et al., "Numerical Simulations of Subsurface Probing in Diffusely Scattering Media Using Spatially Offset Raman Spectroscopy", Applied Spectroscopy, vol. 59, No. 12, 2005.

Schwab, et al., "Versatile, Efficient Raman Sampling with Fiber Optics," Anal. Chem. vol. 56, pp. 2199-2204, 1984.

Cooney, et al., "Comparative Study of Some Fiber-Optic Remote Raman Probe Designs. Part I: Model for Liquids and Transparent Solids," Applied Spectroscopy, vol. 50, No. 7, pp. 836-848 1996.

Cooney, et al., "Comparative Study of Some Fiber-Optic Remote Raman Probe Designs. Part II: Tests for Single-Fiber, Lensed, and Flat-and Bevel-Tip Multi-Fiber Probes," Applied Spectroscopy, vol. 50, No. 7, pp. 849-860 1996.

Office Action for Japanese Application No. 2008-531076 mailed on Apr. 19, 2011.

* cited by examiner

METHOD AND SYSTEM FOR MEASURING SUB-SURFACE COMPOSITION OF A SAMPLE

CROSS-REFERENCE TO RELATED APPLICATIONS

The present application claims the benefit of U.S. Provisional Application No. 60/717,900, entitled "METHOD AND SYSTEM FOR MEASURING SUB-SURFACE COMPOSITION OF A SAMPLE," filed Sep. 16, 2005, which is hereby incorporated by reference herein in its entirety.

STATEMENT REGARDING FEDERALLY SPONSORED RESEARCH OR DEVELOPMENT

This invention was made with government support under AR052010, AR047969 and AR046024 awarded by the National Institutes of Health. The government has certain rights in the invention.

DESCRIPTION OF THE RELATED ART

A globally illuminated fiber optic probe with an array of collection fibers has been used for rapid Raman mapping. An optically similar probe has been employed for pharmaceutical process analysis. Such a probe can be used for efficient signal collection resulting from non-confocality of the globally illuminated probe while binning and co-addition of signals from individual fibers can be used to minimize collection time.

Spatially offsetting the point of signal collection from the point of laser delivery allows discrimination against signals from surface layers and allows collection of spectra from subsurface components. This spatially offset Raman spectroscopy (SORS) can be implemented in most Raman spectroscopy systems. But because a tightly focused laser beam is delivered at a single point, there is a possibility of damage to delicate samples.

SUMMARY OF THE DISCLOSURE

Methods and apparatus are provided for measuring a composition of a sample. First, a surface of the sample is irradiated using a light source. Then, light scattered, reflected, or transmitted by the sample at a variety of locations is received. Next, spectral content information for the received light is determined. The spectral content information is used, at least in part, to determine composition information corresponding to a sub-surface region of the sample.

In one embodiment, a method for measuring a composition of a sample may comprise irradiating an illumination surface area of the sample using a light source, and receiving light from a plurality of emitting surface areas of the sample, each emitting surface area at a different location, the received light scattered by the sample. A cumulative area of the illumination surface area may be greater than a cumulative area of two emitting surface areas of the plurality of emitting surface areas. The method may also include, for each emitting surface area, determining spectral content information associated with received light corresponding to that emitting surface area, and determining composition information corresponding to a sub-surface region of the sample based on the determined spectral content information.

In another embodiment, an apparatus for measuring a composition of a sample, may include an illumination system to illuminate an illumination surface area of the sample, and a plurality of light receivers to receive light from a plurality of emitting surface areas of the sample, each emitting surface area at a different location, the received light scattered by the sample. A cumulative area of the illumination surface area may be greater than a cumulative area of two emitting surface areas of the plurality of emitting surface areas. The apparatus additionally may include a spectrum analyzer optically coupled to receive light received by the plurality of light receivers, the spectrum analyzer configured to generate corresponding spectral content information associated with each emitting surface area of the sample, and a computing device communicatively coupled to the spectrum analyzer, the computing device configured to determine composition information corresponding to a sub-surface region of the sample based on the generated spectral content information.

BRIEF DESCRIPTION OF THE DRAWINGS

The features and advantages of the apparatus and methods described herein will be best appreciated upon reference to the following detailed description and the accompanying drawings, in which.

DETAILED DESCRIPTION

Figure 1:
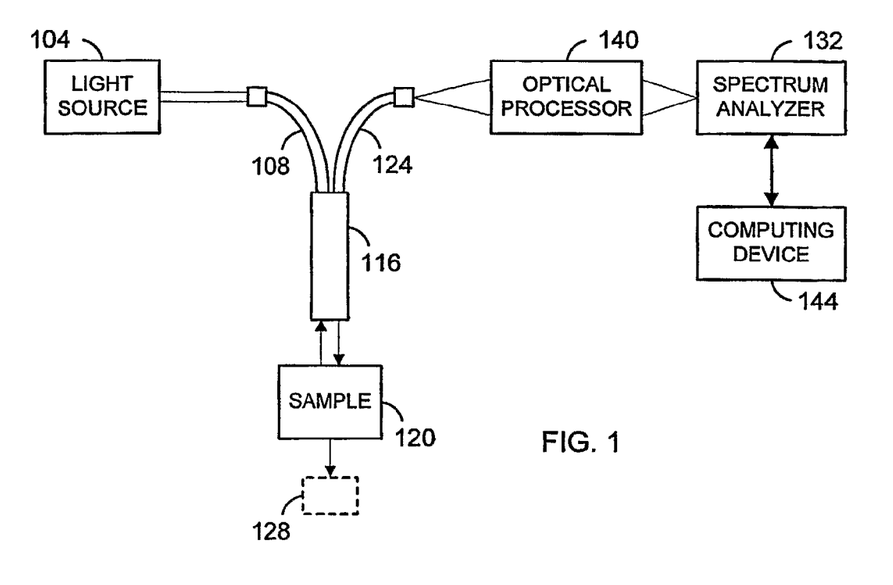
FIG. 1 is a block diagram of one embodiment of an apparatus for measuring a composition of a sample.

FIG. 1 is a block diagram of an example apparatus 100 that may be used to help determine a composition of a sub-surface region of a sample. For example, the apparatus 100 may be used to help determine a composition of a sub-surface region of human or animal tissue, pharmacological products, semiconductor products, etc.

The apparatus 100, which may be used for a Raman spectrometry analysis or an infrared (IR) analysis, for example, includes a light source 104 optically coupled to at least one optical fiber 108. For Raman spectrometry, the light source 104 may comprise a laser, for example, that generates substantially monochromatic light. The optical fiber 108 is optically coupled to an optical probe 116. The optical probe 116 may be positioned proximate to a sample 120, and may be used to irradiate the sample 120 with the light generated by the light source 104. The light source 104, the optical fiber 108, and portions of the optical probe 116 related to illuminating the sample 120 may be components of one embodiment of an illumination system.

In one embodiment, the optical probe 116 is also optically coupled to a plurality of optical fibers 124 (depicted in FIG. 1 as only one optical fiber 124). In this embodiment, the optical probe 116 may be used to collect light scattered, transmitted or reflected by the sample 120 and to transmit the scattered light through the optical fibers 124. This embodiment may be used for Raman spectrometry or for transmission or diffuse reflection IR spectrometry.

In another embodiment, a plurality of optical probes 128 (depicted in FIG. 1 as only one optical fiber 128) may be positioned proximate to the sample 120 such that the optical probes 128 can collect light transmitted by the sample 120. The optical probes 128 may be optically coupled to the optical fibers 124 and can transmit the light transmitted by the sample 120 through the optical fibers 124. This embodiment may be used for "line of sight" IR spectrometry.

The optical fibers 124 are optically coupled to a spectrum analyzer 132 via an optical processor 140 which may include one or more lenses and/or one or more filters. The spectrum analyzer 132 may include, for example, a spectrograph optically coupled to an array of optical detectors, and is communicatively coupled to a computing device 144. The optical fibers 124 are optically coupled to the spectrum analyzer 132 via slit, for example. The detector may comprise a charge coupled device (CCD), for example.

The probe 116 may comprise a plurality of collection optical fibers corresponding to the plurality of optical fibers 124 packed in a generally circular arrangement. The plurality of collection optical fibers may collect light scattered by the sample. The probe 116 may also comprise one or more illumination optical fibers for illuminating the sample 120. The probe 116 may include a lens. In other embodiments, the plurality of collection optical fibers and the one or more illumination optical fibers may be housed in separate probes. Also, the sample 120 need not be illuminated via optical fibers, but may be illuminated by a variety of other techniques such as techniques known to those of ordinary skill in the art.

Figure 2:
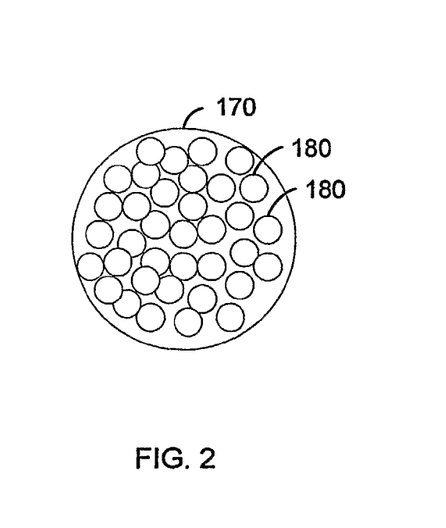
FIG. 2 is a diagram depicting illumination and collection surface areas on a sample.

FIG. 2 is a diagram depicting illumination and collection areas on the sample 120 achieved by one embodiment of a system for determining a composition of the sample 120. For explanatory purposes, FIG. 2 will be described with reference to FIG. 1. The area indicated by the circle 170 corresponds to an illumination area on the surface of the sample 120. Thus, the probe 116 may be configured to illuminate a surface area of the sample 120 corresponding to the area 170. The area indicated by the circle 170 may be referred to as the illumination surface area. In some embodiments, the illumination surface area 170 should be illuminated generally uniformly. In other embodiments, however, the illumination surface area 170 may be illuminated non-uniformly. In these embodiments, the actual distribution of light intensity should be determined or estimated.

The areas indicated by the circles 180 correspond to areas on the surface of the sample 120 from which light will be collected by the plurality of collection optical fibers. In particular, each circle 180 corresponds to a surface area of the sample 120 from which a particular collection fiber will collect light scattered by the sample 120. Each area indicated by one of the circles 180 may be referred to as an emitting surface area. As can be seen in FIG. 2, the emitting surface areas 180 generally form an overall circular shape that is coincident with the circle 170. It will be appreciated that the collection fiber arrangement indicated by FIG. 2 is merely one example of many possible arrangements that may be utilized. For example, different shapes generally formed overall by the plurality of emitting surface areas 180 may be utilized. Also, the shape generally formed overall by the plurality of emitting surface areas 180 may be concentric with or off center from the illumination surface area 170. Some of the emitting surface areas 180 may overlap with one or more other emitting surface areas 180. In some embodiments, each emitting surface area 180 will not overlap with another emitting surface area 180.

Many laser beams have a circular or nearly circular cross-section. Therefore, it may be convenient to approximate the illuminated region as circular and to pack the collection fibers in a manner that approximates a circular array at the collection/sample end of the probe. However, other shapes of illumination surface areas and other shapes generally formed by the plurality of emitting surface areas may be utilized. Different shapes may be advantageous for various specimen or sample geometries or illumination sources, for instance. As just one example, the input laser beam may be shaped into a rectangle and a rectangle of collection fibers of similar aspect ratio could be used. Examples of other shapes that could be utilized include an oval, a square, a rectangle, a triangle, a crescent, a cross, a cross-hatch, etc.

Referring again to FIG. 1, in one embodiment, the spectrum analyzer 132 may comprise an imaging spectrograph. The optical fibers 124 may be arranged in a line at their ends that are coupled to the probe 116. In this way, light corresponding to the optical fibers 124 may be presented to an entrance slit of the imaging spectrograph. The optical fibers 124 may also be arranged in a geometry so that they generate a line image on the imaging plane of a fast spectrograph.

The number of collection fibers used will depend upon various factors, such as one or more of the particular spectrum analyzer 132 used, the thickness of the sample 120, the spatial resolution needed for the measurement, etc. The maximum number of fibers that can be used may depend on a variety of factors such as the fiber core diameter, cladding, thickness, the particular spectrum analyzer 132 to be used, cost, etc. As just one example, if collection fibers having 62 micron core diameter and 125 micron core plus cladding diameter are used, then approximately 50 fibers can be used with a conventional 256 row detector with pixels dimensions of 25 microns square and a spectrograph with a 1:1 magnification.

Figure 3:
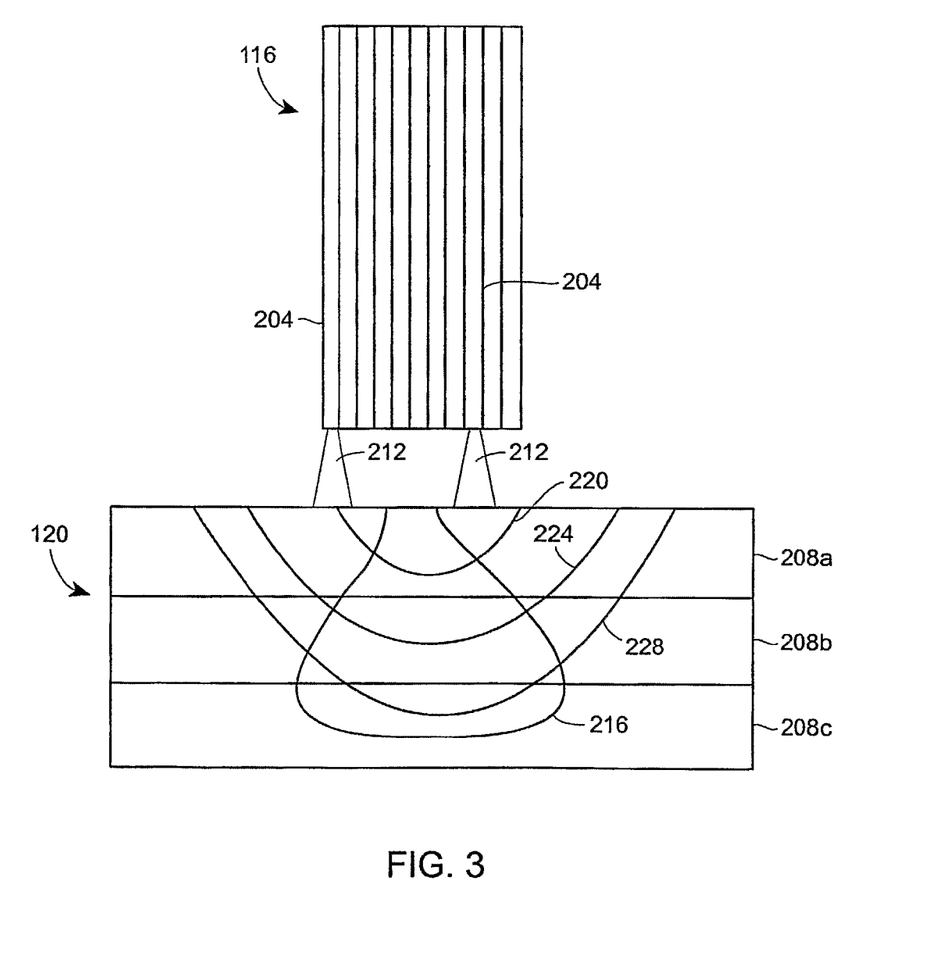
FIG. 3 is a diagram of a probe and a sample showing light scattering within the sample and scattered light being collected by the probe.

Operation of the system 100 will be described with reference to FIG. 3, which includes an illustration of the scattering of light within the sample 120. As describe above, the probe 116 may include a plurality of collection fibers 204. The probe 116 is proximate to the sample 120, which may comprise several different regions 208a, 208b, and 208c. Each collection fiber 204 views a generally conical region 212 whose apex is at the probe end. Each collection fiber 204 is therefore viewing a generally different region of the surface of the sample 120. It is well-known that as laser light penetrates a translucent or turbid object, the light is multiply scattered and the beam spreads out within the object. The area 212 generally indicates the spreading of a beam incident on the surface of the sample 120. Similarly, this multiple scattering causes a return beam to spread. As a result, light beam scatter originating from a point below the surface of the object emerges from the surface with a spatial distribution that is a function of its depth and of the light scattering properties of the object. Thus, the area 220 generally indicates the spreading of a return beam originating from a point within the region 208a. The area 224 generally indicates the spreading of a return beam originating from a point within the region 208b. The area 228 generally indicates the spreading of a return beam originating from a point within the region 208c. Thus, the amount of light collected by each collection fiber 204 due to light originating from a point below the surface of the sample 120 is a function of depth of the point and the position of the point within the field of view of the probe 116. Using mathematical techniques such as principal components analysis and procedures related to it, the spectrum of the composition of layers or chemical component or subsurface irregularities in the object can be measured, provided that enough of the chemical component, layer or subsurface irregularity is present to cause measurable scattering. For any recovered spectrum the amount and spatial distribution can also be recovered.

In general, the closer a collection fiber is to a point of light injection, the greater the scattered light subsequently received by the collection fiber is from surface components. On the other hand, the farther a collection fiber is from a point of light injection, the greater the scattered light subsequently received by the collection fiber is from sub-surface components.

Generally, composition information for a sub-surface region of the sample 120 can be determined based on spectral content information corresponding to light received by each collection fiber 204. Any of variety of techniques can be used to generate the composition information. For example, any of a variety of multivariate techniques can be utilized. One particular technique that may be used with Raman spectroscopy is band entropy target minimization (BTEM). Generally, the number of collection fibers 204 should equal or exceed the number of spectroscopically distinguishable components of the sample 120. But in some instances, a smaller number of collection fibers 204 can be used. Optionally, other information may be utilized as well such as information indicating the relative positions of emitting surface areas and/or a priori information relating to the general composition of the sub-surface region, such as generally known components.

Optionally, spatial composition information may be determined as well. For example, spatial composition information related to the composition of the sample generally in directions parallel to the surface of the sample may be determined. It should be appreciated that multiple scattering may blur details of the distribution. More complete distribution information can be obtained, if the object is viewed from several different directions or if arrays of collection fibers, each array viewing a different section of the object, are used, for example. Similarly, three-dimensional composition information may be determined as well. Well-known tomographic procedures can be adapted for such purposes, for instance.

Figure 4:
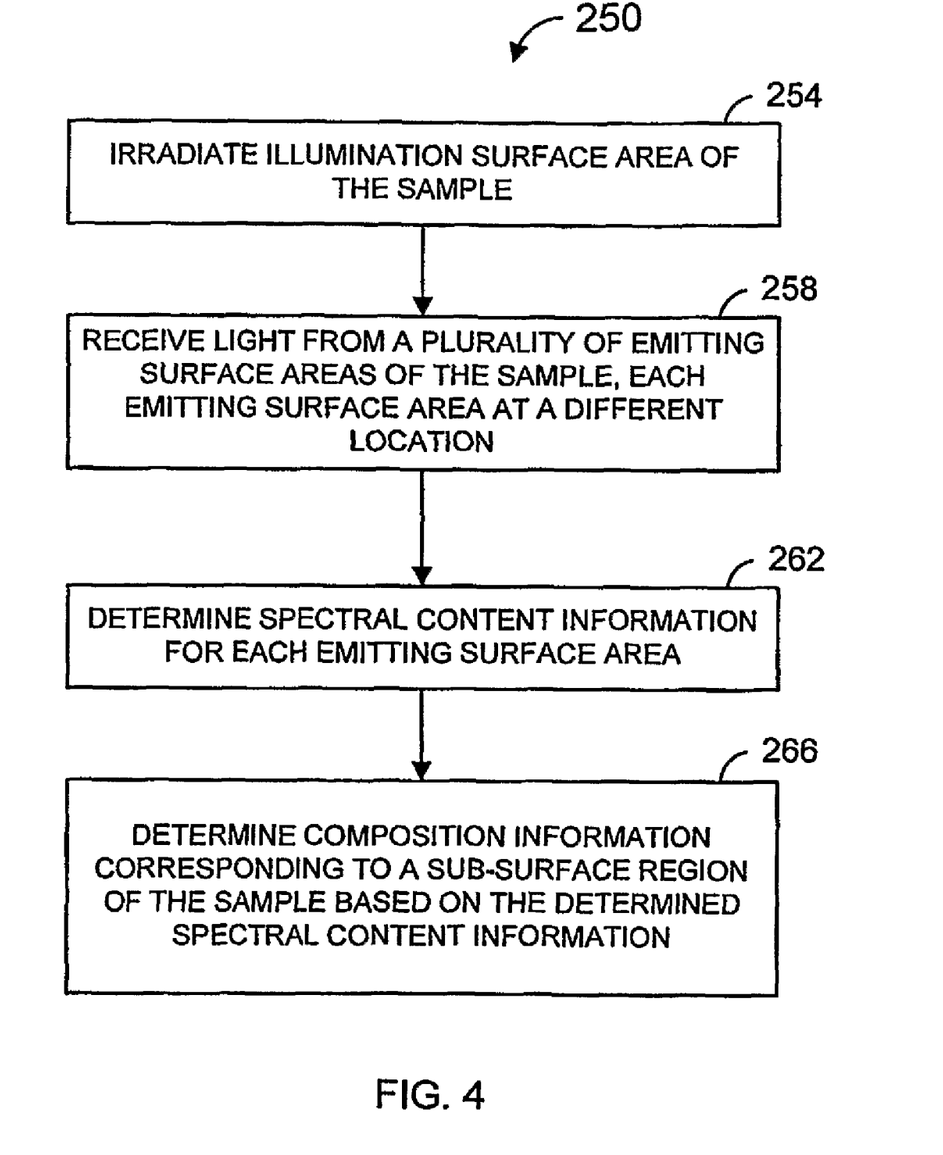
FIG. 4 is a flow diagram of an example method for measuring a composition of a sample.

FIG. 4 is a flow diagram of an example method 250 for measuring a composition of a sample. The method 250 may be implemented by a system such as the system 100 of FIG. 1. At a block 254, an illumination surface area of the sample is irradiated using a light source. Generally, the illumination surface area may be irradiated using unfocused or loosely focused light. At a block 258, light scattered by the sample is received from a plurality of emitting surface areas of the sample. Each emitting surface area may be at a different location. Referring to FIG. 1, each collection fiber in the probe 116 may receive light from a different emitting surface area, for example. Additionally, a cumulative area of the illumination surface area generally should be greater than a cumulative area of two emitting surface areas of the plurality of emitting surface areas. In some implementations, however, the cumulative area of the illumination surface area should be greater than a cumulative area of three, four, five, six, seven, eight, nine, ten, etc., emitting surface areas of the plurality of emitting surface areas. In general, the cumulative area of the illumination surface area may be selected based on zero, one, or more of a variety of factors such as the type of sample, the intensity of the light within the illumination surface area, a desired depth of measurement, a desired resolution, etc.

At a block 262, spectral content information is determined for each emitting surface area based on light received from that emitting surface area. Referring to FIG. 1, the spectrum analyzer 132 may determine spectral content information for each emitting surface area.

At a block 266, composition information corresponding to a sub-surface region of the sample may be determined based on the spectral content information determined at the block 262. Referring to FIG. 1, the computing device 144 may determine the composition information using information received from the spectrum analyzer 132, for example.

Optionally, the spectral content information may be preprocessed. Such preprocessing may include zero, one, or more of dark current subtraction, correction for pixel-pixel response variations, correction for wavelength response dependence, slit image curvature correction, etc.

The block 266 can be implemented using a variety of techniques. For example, any of a variety of multivariate techniques such as principal component analysis (PCA) or the like can be utilized. One particular technique that may be used with Raman spectroscopy is band entropy target minimization (BTEM). Other techniques include eigenvector rotation, the simple-to-use interactive self-modeling mixture analysis (SIMPLISMA) approach, interactive principal component analysis (IPCA), orthogonal projection approach-alternating least squares OPA-ALS, multivariate curve resolution-alternating least squares (MCR-ALS), evolving factor analysis (EFA), etc. In general, information in addition to the spectral content information determined at the block 262 optionally may be used to determine the sub-surface composition information. For instance, if known components are generally expected in the sub-surface region and are not generally expected in the surface region, this information may be used to determine composition information for the sub-surface region. Additionally, if known components are generally expected in the sub-surface region, then spectral information corresponding to these components may be utilized.

Additionally or alternatively, position information associated with the plurality of emitting surface areas may be utilized. This may be useful for assessing whether the light collected at a fiber tends to originate from surface components or sub-surface components, for example. Additionally or alternatively, this may be useful for determining 2-dimensional or 3-dimensional spatial composition information, for example.

If BTEM is utilized, determining composition information may comprise selecting a spectral region of interest based on expected components in the sub-surface region. As just one example, if an expected component has intense signals in a certain area in its Raman spectrum, the spectral region of interest may be selected to include this area. Additionally, determining composition information may comprise calculating a covariance matrix for data in the spectral region of interest, and using BTEM to determine spectral information corresponding to components in the sample. For example, the spectral information may comprise spectral factors corresponding to components in the sample and intensities corresponding to the spectral factors. The intensities may be relative intensities, for example.

Referring again to FIG. 2, if spatial information is also desired, intensities of components may be calculated for each of at least some individual emitting surface areas 180. Additionally, the positions of the emitting surface areas 180 may be utilized to help calculate 2-dimensional or 3-dimensional spatial information for components in the sub-surface area of the sample. As just one example, intensities calculated for the individual emitting surface areas 180 and the positions of the emitting surface areas 180 may be used to calculate a 2-dimensional plot indicative of the amounts of the component at different positions within the sub-surface of the sample. Optionally, multiple measurements of the sample may be taken at different positions and computed tomography techniques may be used to help calculate 2-dimensional or 3-dimensional spatial information for components in the sub-surface area of the sample.

Figure 5:
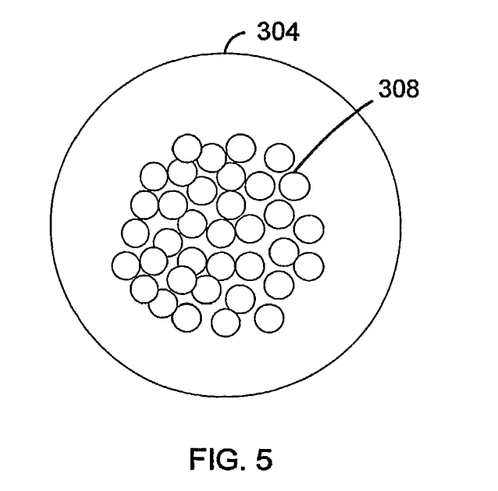
FIG. 5 is a diagram of an example configuration of an illumination area and collection areas that may be used in measuring composition of a sample.
Figure 6:
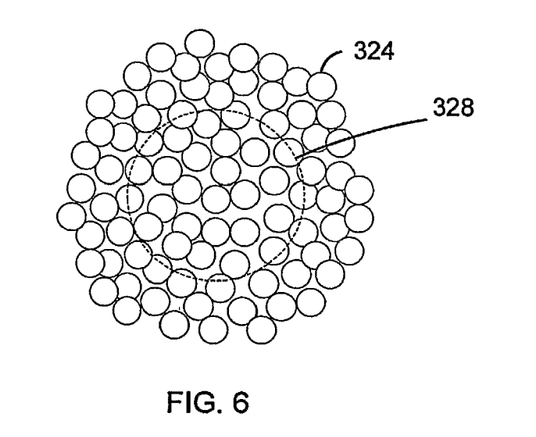
FIG. 6 is a diagram of another example configuration of an illumination area and collection areas that may be used in measuring composition of a sample.

A cumulative surface area of the illumination surface area is generally equal to a cumulative area of the plurality of emitting surface areas. But as described above with respect to FIG. 4, this need not be the case. For instance, the cumulative surface area of the illumination surface area may be merely greater than a cumulative area of two emitting surface areas. Referring to FIG. 5, a cumulative surface area of an illumination surface area 304 may be substantially greater than a cumulative area of the plurality of emitting surface areas 308. Referring to FIG. 6, a cumulative surface area of an illumination surface area 324 may be substantially less than a cumulative area of the plurality of emitting surface areas 328. This arrangement may have a somewhat greater signal/noise ratio than the arrangement of FIG. 2 because there may be less scatter from the surface component in the outer ring, so that light coming from subsurface regions will be a greater proportion of the light collected from outer ring.

Figure 7:
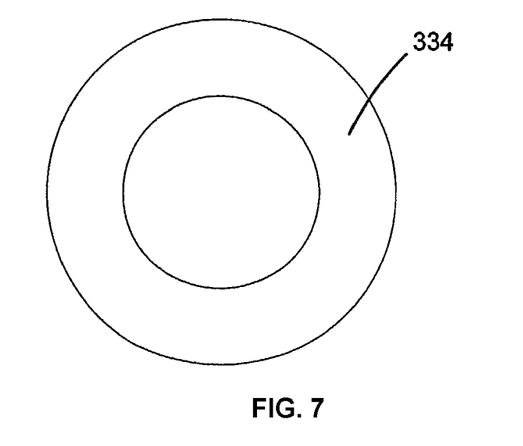
FIG. 7 is a diagram of an example configuration of an illumination area that may be used in measuring composition of a sample.

An illumination surface area may include non-illuminated areas. Thus, as shown in FIG. 7, an illumination surface area 334 may be in the shape of a disc, for example. In general, the illumination surface area may be a variety of patterns including concentric circles, parallel lines, crosses, and other geometric patterns many of which can be generated using inexpensive diffractive optical elements.

Figure 8:
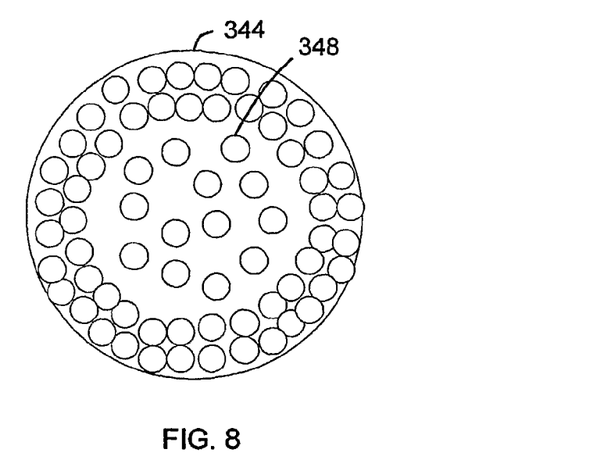
FIG. 8 is a diagram of yet another example configuration of an illumination area and collection areas that may be used in measuring composition of a sample.

Additionally, emitting surface areas need not be uniformly distributed. If emitting surface areas are non-uniformly distributed, this may, in effect, weight the signals from different depths by proportions different from those achieved with a uniform distribution. This may be achieved by non-uniformly distributing collection fibers within a probe, for example. Referring to FIG. 8, within a circular illumination surface area 344, are higher concentration of emitting surface areas 348 are near the edge of the illumination surface area 344 as compared to the center of the illumination surface area 344. By uniformly illuminating the sample, but placing more fibers towards the outer edge of the illuminated region, this may, in effect, more heavily weight signals from the subsurface components. One can envision many variants on this idea. The distribution to be used may depend generally on the composition of the object, for example.

Figure 9:
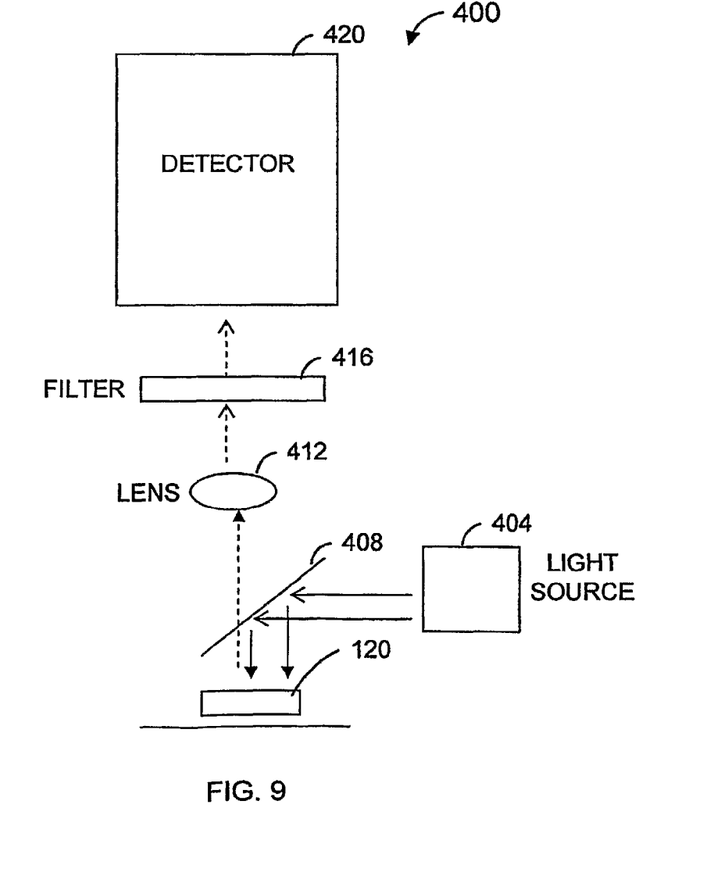
FIG. 9 is a block diagram of another example system that can be utilized to measure a composition of a sample.

FIG. 9 is a block diagram of another example system 400 that can be utilized to determine a composition of a sample. A light source 404 generates light that is reflected from a mirror 408 (e.g., a dichroic mirror) onto the sample 120. The light source 404 and the mirror 408 may be components of an illumination system. In general, an illumination system can be an epi-illumination system, such as is used in fluorescence microscopy, or an oblique illumination system (i.e., light impinging on the sample at an angle), for example.

Light scattered by the sample 120 may pass through the mirror 408 to one or more lenses 412. Then, the scattered light may pass through one or more filters 416 (e.g., a tunable band pass filter). Tunable filters that may be utilized include liquid crystal tunable filters, acousto-optic tunable filters, Fabry-Perot interferometers, Michelson interferometers, etc. The filter 416 should be capable of isolating a band of wavelengths similar in width to typical Raman bands. If fixed filters are used, then at least one filter may be needed for each component expected, and it may be desirable to have three or more filters for each spectral region of interest, so as to do accurate background correction.

Finally, the filtered light is provided to an imaging detector 420. With at least some imaging detectors 420, it may be possible to obtain a high definition image. Detectors that may be utilized include slow scan (also called scientific) charge-coupled detectors, electron-multiplied charge-coupled detectors, intensified charge-coupled detectors, etc.

The example system 400 may utilize a variety of components including well known components, including the ChemImage Falcon II microscope and the Condor (widefield imager). These instruments use liquid crystal tunable filters. However, the detector 420 may have any number of desired pixels. A detector format of 512×512 pixels is widely available, but other sizes (both higher numbers and lower numbers of pixels) can also be used.

The apparatus and methods described above are generally applicable. For example, the apparatus and methods may be used in biomedical application in which target tissue is located close to the skin or to other epithelial tissue such as bone tissue, cartilage tissue, esophagus tissue, colon tissue, etc. In such applications, information regarding components of tissue underneath the skin may be determined. The apparatus and methods may also be used with tumor identification where the potential tumor is located beneath a surface tissue. Similarly, a miniaturized probe can be inserted in a biopsy needle, allowing minimally invasive imaging of tissue that is too deep for transcutaneous imaging. Imaging of bone tissue in the hip is an example of such an application. Alternatively, the method can be combined with conventional arthroscopy to enable better diagnostics of osteoarthritis in the knee joint.

The apparatus and methods described above may be used to evaluate a connective tissue condition (e.g., a bone condition, a cartilage condition, etc.). Examples of connective tissue that can be analyzed include supporting connective tissue (e.g., bone, cartilage, etc.), fibrous connective tissue (e.g., cartilage, tendons, ligaments, etc.), loose connective tissue, adipose tissue, etc. For instance, Raman band areas of various bone or cartilage components can be determined and processed to help generate an indicator of a condition of bone or cartilage tissue. Particular band areas such as a phosphate $v_1$ band area, a carbonate $v_1$ band area, and/or a matrix collagen amide-I band area could be determined and used to analyze the condition of the bone or cartilage tissue. For instance, a carbonate $v_1$ band area to phosphate $v_1$ band area ratio could be determined, as well as a phosphate $v_1$ band area to collagen amide-I band area ratio, and one or both of these ratios could be used to analyze the condition of the bone or cartilage tissue. Further methods and techniques that could be used are described in U.S. patent application Ser. No. 10/944,518, filed Sep. 17, 2004, and entitled "METHOD AND APPARATUS FOR EVALUATING CONNECTIVE TISSUE CONDITIONS." This application is hereby incorporated by reference herein in its entirety.

There are non-medical applications as well. For example, the apparatus and methods may be used to map the distribution of the active pharmaceutical ingredient in coated tablets. It can also be used to identify and characterize the depth of corrosion of metals that have been painted or otherwise coated with a material that scatters light.

There are also applications to laminated or other composite materials. These are frequently constructed from materials such as polymers, that scatter light. Therefore, it is possible to image through the top layer or even several layers and characterize the material in each layer. Another application is to fiber-reinforced composites. Again, the depth penetration allows characterization of the fibers or the surrounding material. As yet another example, the apparatus and methods may be used to analyze semiconductor devices, wafers, etc. One of ordinary skill in the art will recognize many other applications.

Referring again to FIG. 1, many types of light sources 104 may be employed. With regard to Raman spectrometry, a substantially monochromatic light source can be used. In general, near-infrared wavelengths provide better depth of penetration into tissue. On the other hand, as wavelengths increase, they begin to fall outside the response range of silicon photo detectors (which have much better signal-to-noise ratios than other currently available detectors). One example of a light source that can be used is the widely available 830 nanometer diode laser. As another example, a 785 nanometer diode laser could be used.

Many other wavelengths may be used as well. In general, a wavelength of a light source may be chosen based oil various factors including one or more of a desired depth of penetration, availability of photo detectors capable of detecting light at and near the wavelength, efficiency of photo detectors, cost, manufacturability, lifetime, stability, scattering efficiency, penetration depth, etc. Any of a variety of substantially monochromatic light sources can be used, including commercially available light sources. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier. With regard to IR spectrometry, any of a variety of types of light sources can be used, including commercially available light sources.

Existing commercially available fiber optic probes may be used or may be modified, or new probes developed, to maximize collection efficiency of light originating at depths of 1 millimeter or more below the surface of a highly scattering medium, such as biological tissue. Such modified, or newly developed probes, may offer better signal-to-noise ratios and/or faster data collection. The probe may be modified or may be coupled to another device to help maintain a constant probe-to-sample distance, which may help to keep the system in focus and help maximize the collected signal.

If the sample is biological tissue to be irradiated via an incision (and/or the light is to be collected via an incision), relay optics may be coupled to, or incorporated in, a needle or surgical probe. The diameter of the excitation/collection lens or lenses used in such an embodiment could be small to help minimize the size of the incision.

The optical processor 140 may include one or more lenses for focusing the collected light. The optical processor 140 may also include one or more filters to attenuate laser light. Although shown separate from the spectrum analyzer 132, some or all of the optical processor 140 may optionally be a component of the spectrum analyzer 132.

The spectrum analyzer 132 may comprise a spectrograph optically coupled with a photo detector array. The photo detector array may comprise a charge coupled device, or some other photo detection device. For example, the article "Near-infrared multichannel Raman spectroscopy toward real-time in vivo cancer diagnosis," by S. Kaminaka, et al. (Journal of Raman Spectroscopy, vol. 33, pp. 498-502, 2002) describes using a 1064 nanometer wavelength light source with an InP/InGaAsP photomultiplier.

In another embodiment, the spectrum analyzer 132 may comprise one or more filters to isolate a plurality of wavelengths of interest. Then, one or more photo detectors (e.g., a CCD, an avalanche photodiode, photomultiplier tube, etc.) could be optically coupled to the output of each filter. A single detector could be used with a tunable filter (e.g., an interferometer, liquid crystal tunable filter, acousto-optic tunable filter, etc.) or if fixed passband filters (e.g., dielectric filters, holographic filters, etc.) are placed in front of the detector one at a time using, for example, a slider, filter wheel, etc. In general, any of a variety of spectrum analyzers could be used such as a Raman analyzer, an IR spectrum analyzer, an interferometer, etc.

The computing device 144 may comprise, for example, an analog circuit, a digital circuit, a mixed analog and digital circuit, a processor with associated memory, a desktop computer, a laptop computer, a tablet PC, a personal digital assistant, a workstation, a server, a mainframe, etc. The computing device 144 may be communicatively coupled to the spectrum analyzer 132 via a wired connection (e.g., wires, a cable, a wired local area network (LAN), etc.) or a wireless connection (a BLUETOOTH™ link, a wireless LAN, an IR link, etc.). In some embodiments, the spectral content information generated by the spectrum analyzer 132 may be stored on a disk (e.g., a floppy disk, a compact disk (CD), etc.), and then transferred to the computing device 144 via the disk. Although the spectrum analyzer 132 and the computer 144 are illustrated in FIG. 1 as separate devices, in some embodiments the spectrum analyzer 132 and the computing device 144 may be part of a single device. For example, the computing device 144 (e.g., a circuit, a processor and memory, etc.) may be a component of the spectrum analyzer 132.

Figure 10:
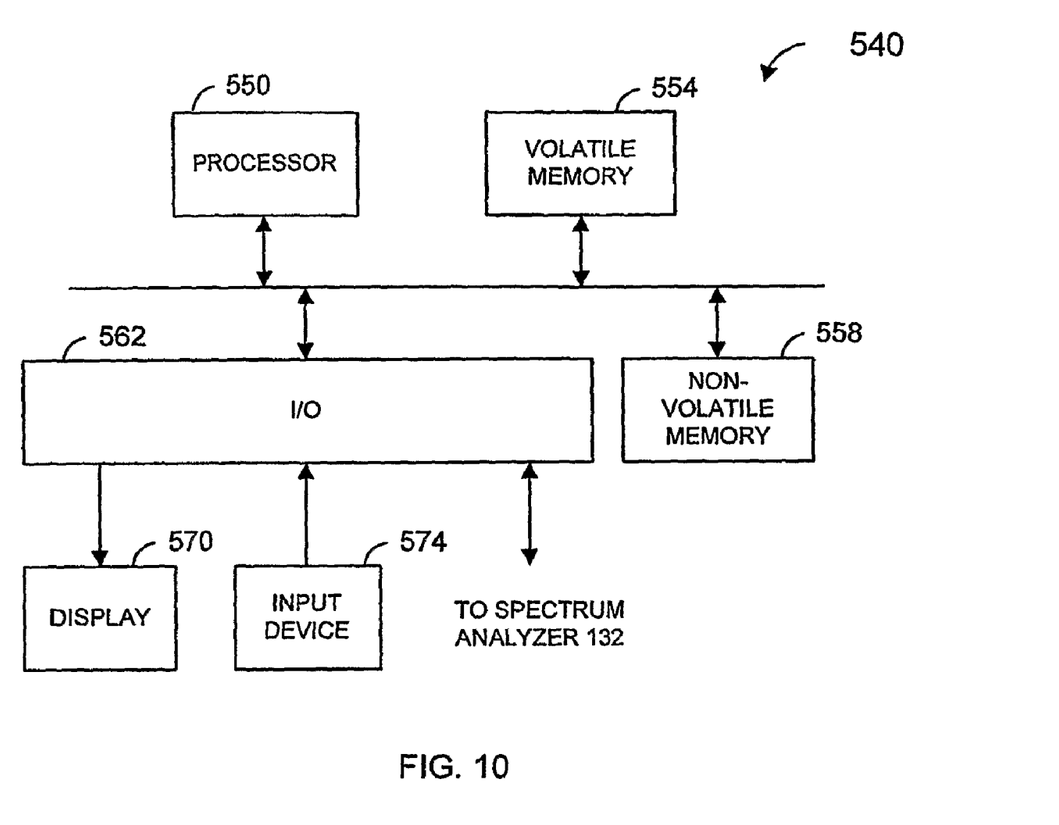
FIG. 10 is a block diagram of an example computer that can be used with the apparatus of FIG. 1.

FIG. 10 is a block diagram of an example computing device 144 that may be employed. It is to be understood that the computer 540 illustrated in FIG. 10 is merely one example of a computing device 144 that may be employed. As described above, many other types of computing devices 144 may be used as well. The computer 540 may include at least one processor 550, a volatile memory 554, and a non-volatile memory 558. The volatile memory 554 may include, for example, a random access memory (RAM). The non-volatile memory 558 may include, for example, one or more of a hard disk, a read-only memory (ROM), a CD-ROM, an erasable programmable ROM (EPROM), an electrically erasable programmable ROM (EEPROM), a digital versatile disk (DVD), a flash memory, etc. The computer 540 may also include an I/O device 562. The processor 550, volatile memory 554, non-volatile memory 558, and the I/O device 562 may be interconnected via one or more address/data buses 566. The computer 540 may also include at least one display 570 and at least one user input device 574. The user input device 574 may include, for example, one or more of a keyboard, a keypad, a mouse, a touch screen, etc. In some embodiments, one or more of the volatile memory 554, non-volatile memory 558, and the I/O device 562 may be coupled to the processor 550 via one or more separate address/data buses (not shown) and/or separate interface devices (not shown), coupled directly to the processor 550, etc.

The display 570 and the user input device 574 are coupled with the I/O device 562. The computer 540 may be coupled to the spectrum analyzer 132 (FIG. 1) via the I/O device 562. Although the I/O device 562 is illustrated in FIG. 10 as one device, it may comprise several devices. Additionally, in some embodiments, one or more of the display 570, the user input device 574, and the spectrum analyzer 132 may be coupled directly to the address/data bus 566 or the processor 550. Additionally, as described previously, in some embodiments the spectrum analyzer 132 and the computer 540 may be incorporated into a single device.

A routine, for example, for determining a measurement of composition of a sample in a sub-surface region may be stored, for example, in whole or in part, in the non-volatile memory 558 and executed, in whole or in part, by the processor 550. For example, the block 266 of FIG. 4 could be implemented in whole or in part via a software program for execution by the processor 550. The program may be embodied in software stored on a tangible medium such as CD-ROM, a floppy disk, a hard drive, a DVD, or a memory associated with the processor 550, but persons of ordinary skill in the art will readily appreciate that the entire program or parts thereof could alternatively be executed by a device other than a processor, and/or embodied in firmware and/or dedicated hardware in a well known manner.

With regard to the method 200 of FIG. 4, one of ordinary skill in the art will recognize that the order of execution of the blocks may be changed, and/or the blocks may be changed, eliminated, or combined.

Although block 266 of FIG. 4 was described above as possibly being implemented by the computer 540, it could also be implemented, at least partially, by other types of devices such as an analog circuit, a digital circuit, a mixed analog and digital circuit, a processor with associated memory, etc.

At least portions of the techniques described above, including the blocks described with reference to FIG. 4, may be implemented using software comprising computer program instructions. Such computer program instructions may control the operation of a computing device such as a desktop computer, a laptop computer, a tablet computer, a workstation, a server, a mainframe, a cellular phone, a telephone, a set top box, a PDA, a pager, a processing system of an electronic toy, a processing system of an electronic game, a processing system of a consumer electronics device, etc. The computing device may have a memory in which the computer program instructions may be stored. The computer program instructions may be written in any high level language such as the programming language used with MATHEMATICA® software systems, C, C++, C#, Java or the like or any low-level assembly or machine language. By storing computer program instructions in a memory of the computing device, the computing device is physically and/or structurally configured in accordance with the computer program instructions.

While many methods and systems have been described herein as being implementable in software, they may be implemented in hardware, firmware, etc., and may be implemented by a variety of computing systems and devices. Thus, the method blocks and system blocks described herein may be implemented in a standard multi-purpose central processing unit (CPU), a special purpose CPU, or on specifically designed hardware or firmware such as an application-specific integrated circuit (ASIC) or other hard-wired device as desired. When implemented in software, the software routine may be stored in any computer readable memory such as on a magnetic disk, a laser disk (such as a compact disk (CD), a digital versatile disk (DVD)), a flash memory, a memory card, a memory stick, etc., or other storage medium, in a RAM or ROM of a computer or processor, in any database, etc. Likewise, this software may be delivered via any known or desired delivery method including, for example, on a computer readable memory or other transportable computer storage mechanism or over a communication channel such as a telephone line, the internet, etc. (which are viewed as being the same as or interchangeable with providing such software via a transportable storage medium).

Figure 11:
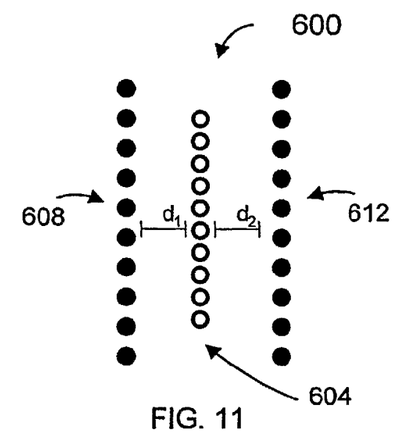
FIG. 11 is a diagram of an example probe configuration.

Although examples of probes have been described above, one of ordinary skill in the art will recognize many other probe configurations may be utilized as well. FIGS. 11-22 provide illustrations of examples of other probe configurations that may be utilized. FIG. 11 is a diagram of a probe configuration 600. The probe configuration 600 includes a group of illumination fibers 604, a group of collection fibers 608 and a group of collection fibers 612. Depending upon the particular implementation, the illumination surface area corresponding to the group of illumination fibers 604 will be substantially in the shape of a line or a line of circles, and the illumination surface area may be contiguous or non-contiguous. The group of collection fibers 608 may be spaced apart from the group of illumination fibers 604 by a space $d_1$, and the group of collection fibers 612 may be spaced apart from the group of illumination fibers 604 by a space $d_2$. In general, the distance $d_1$ should be different than the distance $d_2$, although in some implementations if may be appropriate for the distances to be substantially equal.

Figure 12:
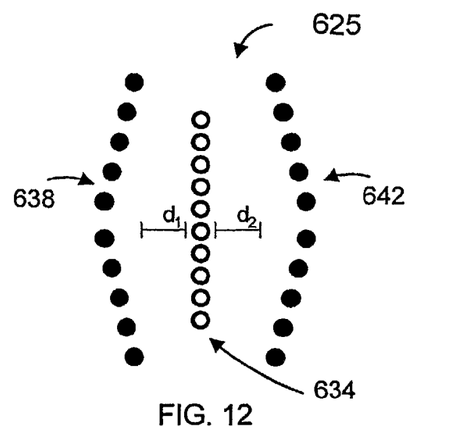
FIG. 12 is a diagram of another example probe configuration.

FIG. 12 is a diagram of a probe configuration 625. The probe configuration 625 includes a group of illumination fibers 634, a group of collection fibers 638 and a group of collection fibers 642. Depending upon the particular implementation, the illumination surface area corresponding to the group of illumination fibers 604 will be substantially in the shape of a line or a line of circles, and the illumination surface area may be contiguous or non-contiguous. The group of collection fibers 638 and the group of collection fibers 642 may each be in the general shape of a "V" or a semicircle. As with the configuration 600 of FIG. 11, the group of collection fibers 638 may be spaced apart from the group of illumination fibers 634 by the space $d_1$, and the group of collection fibers 642 may be spaced apart from the group of illumination fibers 634 by the space $d_2$.

Figure 13:
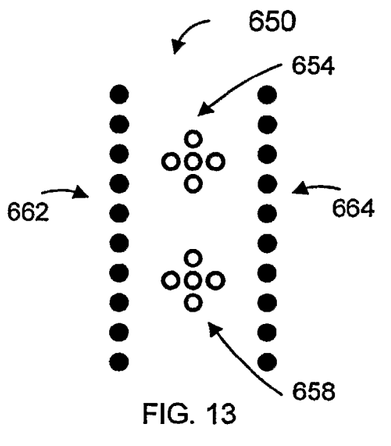
FIG. 13 is a diagram of another example probe configuration.

FIG. 13 is a diagram of a probe configuration 650. The probe configuration 650 includes a group of illumination fibers 654, a group of illumination fibers 658, a group of collection fibers 662 and a group of collection fibers 664. Depending upon the particular implementation, the illumination surface areas corresponding to the groups of illumination fibers 654 and 658 each will be substantially in the shape of a cross or circles arranged in a cross, and the illumination surface areas may be contiguous or non-contiguous. The groups of collection fibers 664 and 668 may be at different distances from the groups of illumination fibers 654 and 658, similar to the configurations 600 and 625 of FIGS. 11 and 12.

Figure 14:
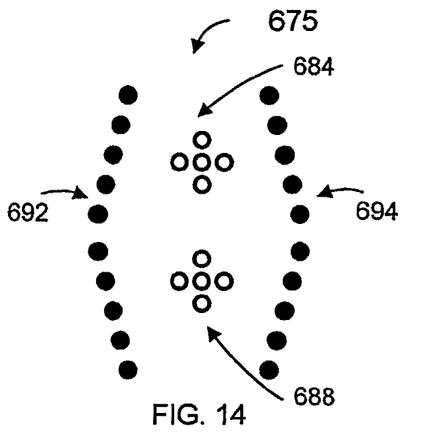
FIG. 14 is a diagram of another example probe configuration.

FIG. 14 is a diagram of a probe configuration 675. The probe configuration 675 includes a group of illumination fibers 684, a group of illumination fibers 688, a group of collection fibers 692 and a group of collection fibers 694. Depending upon the particular implementation, the illumination surface areas corresponding to the groups of illumination fibers 654 and 658 each will be substantially in the shape of a cross or circles arranged in a cross, and the illumination surface areas may be contiguous or non-contiguous. The group of collection fibers 692 and the group of collection fibers 694 may each be in the general shape of a "V" or a semicircle. The groups of collection fibers 692 and 694 may be at different distances from the groups of illumination fibers 684 and 688, similar to the configurations 600 and 625 of FIGS. 11 and 12.

Figure 15:
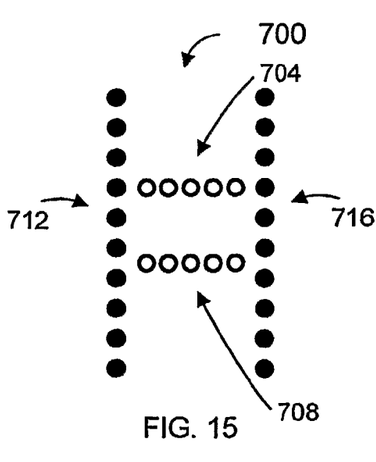
FIG. 15 is a diagram of another example probe configuration.

FIG. 15 is a diagram of a probe configuration 700. The probe configuration 700 includes a group of illumination fibers 704, a group of illumination fibers 708, a group of collection fibers 712 and a group of collection fibers 716. Depending upon the particular implementation, the illumination surface areas corresponding to the groups of illumination fibers 704 and 708 each will be substantially in the shape of a line or circles arranged in a line, and the illumination surface areas may be contiguous or non-contiguous. For example, the illumination surface areas corresponding to the groups of illumination fibers 704 and 708 may be two separate generally shaped lines or a contiguous rectangle. The lines formed by the groups of illumination fibers 704 and 708 may be substantially perpendicular to the lines formed by the groups of collection fibers 712 and 716. Alternatively, the lines formed by the groups of illumination fibers 704 and 708 may be at a small angle from perpendicular (e.g., at an angle approximately 5 degrees from perpendicular) with respect to the lines formed by the groups of collection fibers 712 and 716. The groups of collection fibers 712 and 716 may be at different distances from the groups of illumination fibers 704 and 708, similar to the configurations 600 and 625 of FIGS. 11 and 12.

Figure 16:
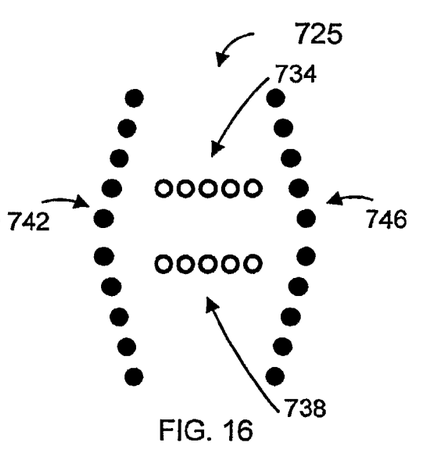
FIG. 16 is a diagram of another example probe configuration.

FIG. 16 is a diagram of a probe configuration 725. The probe configuration 725 includes a group of illumination fibers 734, a group of illumination fibers 738, a group of collection fibers 742 and a group of collection fibers 746. The illumination surface areas corresponding to the groups of illumination fibers 734 and 738 may be similar to the illumination surface areas corresponding to the groups of illumination fibers 704 and 708 in FIG. 15. The group of collection fibers 742 and the group of collection fibers 746 may each be in the general shape of a "V" or a semicircle. The groups of collection fibers 742 and 746 may be at different distances from the groups of illumination fibers 734 and 738, similar to the configurations 600 and 625 of FIGS. 11 and 12.

Figure 17:
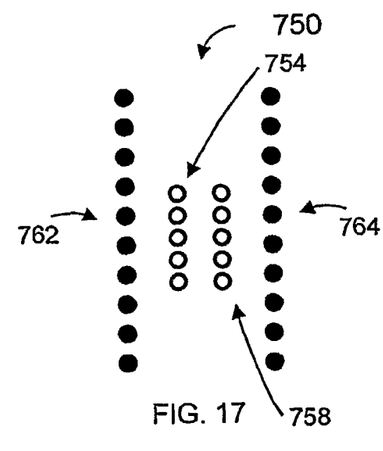
FIG. 17 is a diagram of another example probe configuration.

FIG. 17 is a diagram of a probe configuration 750. The probe configuration 750 includes a group of illumination fibers 754, a group of illumination fibers 758, a group of collection fibers 762 and a group of collection fibers 764. Depending upon the particular implementation, the illumination surface areas corresponding to the groups of illumination fibers 754 and 758 each will be substantially in the shape of a line or circles arranged in a line, and the illumination surface areas may be contiguous or non-contiguous. For example, the illumination surface areas corresponding to the groups of illumination fibers 754 and 758 may be two separate generally shaped lines or a contiguous rectangle. The lines formed by the groups of illumination fibers 754 and 758 may be substantially parallel to the lines formed by the groups of collection fibers 762 and 764. Alternatively, the lines formed by the groups of illumination fibers 754 and 758 may be at a small angle from parallel (e.g., at an angle approximately 5 degrees from parallel) with respect to the lines formed by the groups of collection fibers 762 and 764. The groups of collection fibers 762 and 764 may be at different distances from the groups of illumination fibers 754 and 758, similar to the configurations 600 and 625 of FIGS. 11 and 12.

Figure 18:
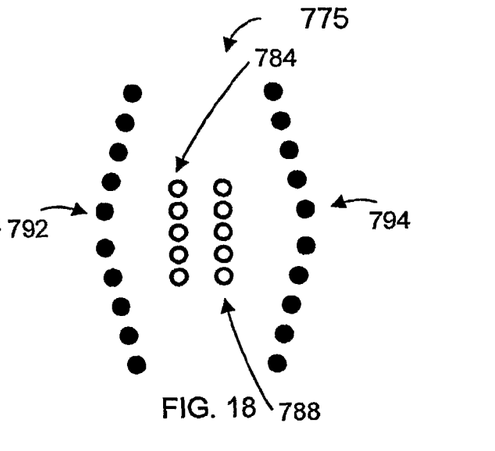
FIG. 18 is a diagram of another example probe configuration.

FIG. 18 is a diagram of a probe configuration 775. The probe configuration 775 includes a group of illumination fibers 784, a group of illumination fibers 788, a group of collection fibers 792 and a group of collection fibers 794. The illumination surface areas corresponding to the groups of illumination fibers 784 and 788 may be similar to the illumination surface areas corresponding to the groups of illumination fibers 754 and 758 in FIG. 17. The group of collection fibers 792 and the group of collection fibers 794 may each be in the general shape of a "V" or a semicircle. The groups of collection fibers 792 and 794 may be at different distances from the groups of illumination fibers 784 and 788, similar to the configurations 600 and 625 of FIGS. 11 and 12.

Figure 19:
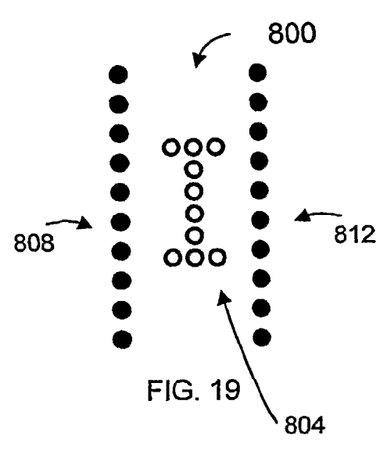
FIG. 19 is a diagram of another example probe configuration.

FIG. 19 is a diagram of a probe configuration 800. The probe configuration 800 includes a group of illumination fibers 804, a group of collection fibers 808 and a group of collection fibers 812. Depending upon the particular implementation, the illumination surface area corresponding to the group of illumination fibers 804 will be substantially in the shape of an "I" or circles arranged in the shape of an "I", and the illumination surface area may be contiguous or non-contiguous. The groups of collection fibers 808 and 812 may be at different distances from the group of illumination fibers 804, similar to the configurations 600 and 625 of FIGS. 11 and 12.

Figure 20:
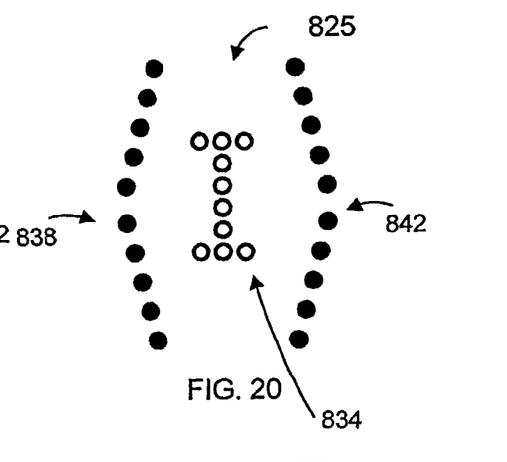
FIG. 20 is a diagram of another example probe configuration.

FIG. 20 is a diagram of a probe configuration 825. The probe configuration 825 includes a group of illumination fibers 834, a group of collection fibers 838 and a group of collection fibers 842. Depending upon the particular implementation, the illumination surface area corresponding to the group of illumination fibers 834 will be substantially in the shape of an "I" or circles arranged in the shape of an "I", and the illumination surface area may be contiguous or non-contiguous. The group of collection fibers 838 and the group of collection fibers 842 may each be in the general shape of a "V" or a semicircle. The groups of collection fibers 838 and 842 may be at different distances from the group of illumination fibers 834, similar to the configurations 600 and 625 of FIGS. 11 and 12.

Figures 21, 22:
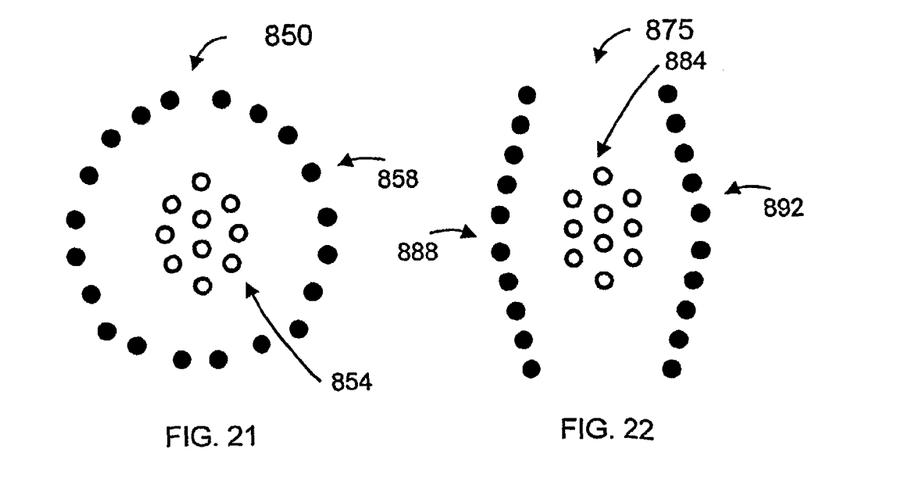
FIG. 21 is a diagram of yet another example probe configuration.
FIG. 22 is a diagram of still another example probe configuration.

FIG. 21 is a diagram of a probe configuration 850. The probe configuration 850 includes a group of illumination fibers 854, a group of collection fibers 858. Depending upon the particular implementation, the illumination surface area corresponding to the group of illumination fibers 854 will be generally in the shape of an oval or circles arranged in the general shape of an oval, and the illumination surface area may be contiguous or non-contiguous. The group of collection fibers 858 may be arranged in the general shape of a circle or oval. In some implementations, the center of the general oval formed by the group of illumination fibers 854 may be non-concentric with the circle or oval formed by the group of collection fibers 858.

FIG. 22 is a diagram of a probe configuration 875. The probe configuration 875 includes a group of illumination fibers 884, a group of collection fibers 888 and a group of collection fibers 892. Depending upon the particular implementation, the illumination surface area corresponding to the group of illumination fibers 854 will be generally in the shape of an oval or circles arranged in the general shape of an oval, and the illumination surface area may be contiguous or non-contiguous. The group of collection fibers 888 and the group of collection fibers 892 may each be in the general shape of a "V" or a semicircle. The groups of collection fibers 888 and 892 may be at different distances from the group of illumination fibers 884, similar to the configurations 600 and 625 of FIGS. 11 and 12.

With regard to the example probe configurations described with respect to FIGS. 11-22, it will be understood that in other implementations, the fibers described as illuminating fibers may be collection fibers, and the fibers described as collection fibers may be illuminating fibers. Additionally, it will be understood that in other implementations the illumination surface areas describe with respect FIGS. 11-22 need not be formed with a plurality of fibers, but instead could be formed by some other technique such as shaping an unfocused or loosely focused beam of light into the desired shape. Further, the numbers of fibers illustrated in FIGS. 11-22 have been reduced for simplicity. Typically, more fibers will be used. For example, as many as 50 collection fibers may be used with many standard spectroscopy configuration charge coupled devices. In general, the number of collection fibers should equal or exceed the number of spectroscopically distinguishable components of the sample. In at least some implementations, the number of illumination fibers and/or the size of the aggregate illumination surface area may be chosen so that the delivered power is distributed sufficiently to prevent damage to the sample.

The present disclosure has been described with reference to specific examples, which are intended to be illustrative only and not to be limiting. It will be apparent to those of ordinary skill in the art that changes, additions or deletions may be made to the disclosed examples without departing from the spirit and scope of the disclosure.

What is claimed is:

1. A method for measuring a composition of a sample, the method comprising:
    irradiating an illumination surface area of the sample using a light source;
    receiving light from a plurality of emitting surface areas of the sample, each emitting surface area at a different location, the received light scattered by the sample;
    wherein a cumulative area of the illumination surface area is greater than a cumulative area of two emitting surface areas of the plurality of emitting surface areas;
    for each emitting surface area, determining spectral content information associated with received light corresponding to that emitting surface area; and
    for each of a plurality of areas of the sample, determining composition information corresponding to a sub-surface region of the sample based on the determined spectral content information for multiple emitting surface areas spaced apart from the area of the sample.

2. A method according to claim 1, wherein the cumulative area of the illumination surface area is substantially the same as a cumulative area of the plurality of surface areas.

3. A method according to claim 1, wherein the cumulative area of the illumination surface area is substantially less than a cumulative area of the plurality of surface areas.

4. A method according to claim 1, wherein the cumulative area of the illumination surface area is substantially greater than a cumulative area of the plurality of surface areas.

5. A method according to claim 1, wherein the cumulative area of the illumination surface area is greater than a cumulative area of five emitting surface areas of the plurality of emitting surface areas.

6. A method according to claim 1, wherein the cumulative area of the illumination surface area is greater than a cumulative area of ten emitting surface areas of the plurality of emitting surface areas.

7. A method according to claim 1, wherein the illumination surface area is one contiguous area.

8. A method according to claim 1, wherein the illumination surface area comprises a plurality of separate areas.

9. A method according to claim 1, wherein irradiating the illumination surface area comprises shaping the illumination surface area.

10. A method according to claim 9, wherein a shape of the illumination surface area comprises at least one of a circle, an oval, a square, a rectangle, a triangle, a line, or a cross.

11. A method according to claim 1, wherein the cumulative area of the illumination surface area overlaps at least partially with at least some of the plurality of surface areas.

12. A method according to claim 1, wherein the cumulative area of the illumination surface area does not overlap with the plurality of surface areas.

13. A method according to claim 1, wherein receiving light from the plurality of emitting surface areas of the sample comprises collecting light using a plurality of optical fibers, each optical fiber corresponding to a different one of the plurality of emitting surface areas.

14. A method according to claim 1, wherein collecting light using the plurality of optical fibers comprises using a probe having optical collection fibers arranged in at least one of a circle, an oval, and at least one line.

15. A method according to claim 14, wherein collecting light using the plurality of optical fibers comprises using a probe having optical collection fibers included within an interior of a circle.

16. A method according to claim 1, wherein receiving light from the plurality of emitting surface areas of the sample comprises detecting light using an array of detectors, each detector in the array of detectors corresponding to a different one of the plurality of emitting surface areas.

17. A method according to claim 1, wherein determining composition information corresponding to the sub-surface region of the sample comprises determining composition information based on spectral information corresponding to expected components in the sub-surface region.

18. A method according to claim 1, further comprising determining spatial composition information corresponding to the sub-surface region of the sample.

19. A method according to claim 18, wherein determining spatial composition information comprises using position information associated with the plurality of emitting surface areas.

20. A method according to claim 16, further comprising:
    determining spatial composition information for the sub-surface region of the sample based on the determined spectral content information.

21. A method according to claim 1, further comprising using position information associated with the plurality of emitting surface areas to assess whether received light associated with a particular emitting surface area originates from surface components of the sample or sub-surface components of the sample.

22. A method according to claim 1, further comprising:
    repeating the acts of irradiating, receiving light, determining spectral content information, and determining composition information for a plurality of different directions; and determining spatial composition information for the sub-surface region of the sample based on the determined spectral content information from the plurality of different directions.

23. A method according to claim 1, further comprising:
repeating the acts of irradiating, receiving light, determining spectral content information, and determining composition information for a plurality of different directions; and
determining three-dimensional composition information for the sub-surface region of the sample based on the determined spectral content information from the plurality of different directions.

24. A method according to claim 1, wherein determining composition information comprises using a multivariate technique.

25. An apparatus for measuring a composition of a sample, comprising:
an illumination system to illuminate an illumination surface area of the sample;
a plurality of light receivers to receive light from a plurality of emitting surface areas of the sample, each emitting surface area at a different location, the received light scattered by the sample;
wherein a cumulative area of the illumination surface area is greater than a cumulative area of two emitting surface areas of the plurality of emitting surface areas;
a spectrum analyzer optically coupled to receive light received by the plurality of light receivers, the spectrum analyzer configured to generate corresponding spectral content information associated with each emitting surface area of the sample; and
a computing device communicatively coupled to the spectrum analyzer, the computing device configured to determine, for each of a plurality of areas of the sample, composition information corresponding to a sub-surface region of the sample based on the generated spectral content information for multiple emitting surface areas spaced apart from the area of the sample.

26. An apparatus according to claim 25, wherein the illumination system is configured to generate the illumination surface area having a cumulative area substantially the same as a cumulative area of the plurality of surface areas.

27. An apparatus according to claim 25, wherein the illumination system is configured to generate the illumination surface area having a cumulative area substantially less than a cumulative area of the plurality of surface areas.

28. An apparatus according to claim 25, wherein the illumination system is configured to generate the illumination surface area having a cumulative area substantially greater than a cumulative area of the plurality of surface areas.

29. An apparatus according to claim 25, wherein the illumination system is configured to generate the illumination surface area having a cumulative area greater than a cumulative area of four emitting surface areas of the plurality of emitting surface areas.

30. An apparatus according to claim 25, wherein the illumination system is configured to generate the illumination surface area having a cumulative area greater than a cumulative area of eight emitting surface areas of the plurality of emitting surface areas.

31. An apparatus according to claim 25, wherein the illumination system is configured to generate the illumination surface area as one contiguous area.

32. An apparatus according to claim 25, wherein the illumination system is configured to generate the illumination surface area as a plurality of separate areas.

33. An apparatus according to claim 25, wherein illumination system comprises a spot shaper to shape the illumination surface area.

34. An apparatus according to claim 33, wherein the illumination system is configured to generate a shape of the illumination surface area including at least one of a circle, an oval, a square, a rectangle, a triangle, a line, an I shape, or a cross.

35. An apparatus according to claim 25, wherein the illumination system is configured to generate the illumination surface area to overlap at least partially with at least some of the plurality of surface areas.

36. An apparatus according to claim 25, wherein the illumination system is configured to generate the illumination surface area to not overlap with the plurality of surface areas.

37. An apparatus according to claim 25, wherein the plurality of light receivers comprises a plurality of optical fibers, each optical fiber corresponding to a different one of the plurality of emitting surface areas.

38. An apparatus according to claim 37, further comprising a probe having the plurality of optical fibers arranged in at least one of a circle, an oval, and at least one line.

39. An apparatus according to claim 38, wherein the optical fibers from the plurality of optical fibers are included within an interior of the circle.

40. An apparatus according to claim 25, wherein the plurality of light receivers comprises an array of detectors, each detector in the array of detectors corresponding to a different one of the plurality of emitting surface areas.

41. An apparatus according to claim 25, wherein the computing device is configured to determine composition information based on spectral information corresponding to expected components in the sub-surface region.

42. An apparatus according to claim 25, wherein the computing device is further configured to determine spatial composition information corresponding to the sub-surface region of the sample.

43. An apparatus according to claim 25, wherein the computing device is further configured to determine spatial composition information using position information associated with the plurality of emitting surface areas.

44. An apparatus according to claim 40, wherein the computing device is configured to determine spatial composition information for the sub-surface region of the sample based on the determined spectral content information.

45. An apparatus according to claim 25, wherein the computing device is further configured to use position information associated with the plurality of emitting surface areas to assess whether received light associated with a particular emitting surface area originates from surface components of the sample or sub-surface components of the sample.

46. An apparatus according to claim 25, wherein the computing device is configured to determine spatial composition information for the sub-surface region of the sample based on determined spectral content information corresponding to irradiating the sample from a plurality of different directions.

47. An apparatus according to claim 25, wherein the computing device is configured to determine three-dimensional composition information for the sub-surface region of the sample based on determined spectral content information corresponding to irradiating the sample from a plurality of different directions.

48. An apparatus according to claim 25, wherein the computing device is configured to determine using a multivariate technique.

* * * * *

UNITED STATES PATENT AND TRADEMARK OFFICE
CERTIFICATE OF CORRECTION

PATENT NO. : 8,054,463 B2
APPLICATION NO. : 12/066915
DATED : November 8, 2011
INVENTOR(S) : Michael D. Morris et al.

Page 1 of 1

It is certified that error appears in the above-identified patent and that said Letters Patent is hereby corrected as shown below:

At Column 18, line 7, "line, an I shape, or" should be -- line, or --.

Signed and Sealed this
Thirteenth Day of November, 2012

David J. Kappos
*Director of the United States Patent and Trademark Office*